United States Patent [19]
Muraoka et al.

[11] Patent Number: 6,043,217
[45] Date of Patent: Mar. 28, 2000

[54] AMIDE DERIVATIVE OF AMYTHIAMICIN

[75] Inventors: Yasuhiko Muraoka, Tokyo; Hironobu Iinuma, Yokohama; Tomio Takeuchi, Tokyo; Tsuneo Okonogi, Yokohama, all of Japan

[73] Assignee: Zaidan Hojin Biseibutsu Kagaku Kenyu Kai, Tokyo, Japan

[21] Appl. No.: 08/915,118

[22] Filed: Aug. 20, 1997

[30] Foreign Application Priority Data

Aug. 22, 1996 [JP] Japan ..................................... 8-221476

[51] Int. Cl.⁷ .............................. A61K 38/00; C07K 5/00
[52] U.S. Cl. ................................................ 514/9; 530/317
[58] Field of Search .................. 514/9; 530/317

[56] References Cited

PUBLICATIONS

Shimanaka et al., J. Antibiotics, vol. 47, No. 6, pp. 668–674, 1994.
Shimanaka et al., J. Antibiotics, vol. 47, No. 6, pp. 1145–1152, 1994.
Shimanaka et al., J. Antibiotics, vol. 47, No. 6, pp. 1153–1159, 1994.

*Primary Examiner*—Raymond Henley, III
*Attorney, Agent, or Firm*—Birch, Stewart, Kolasch & Birch, LLP

[57] ABSTRACT

Novel amide derivatives of amythiamicin are now provided, which are soluble in water and exhibit antibacterial activities, some of which exhibit an excellent antibacterial activity against methicillin-resistant *Staphylococcus aureus* (MRSA).

14 Claims, No Drawings

AMIDE DERIVATIVE OF AMYTHIAMICIN

TECHNICAL FIELD OF THE INVENTION

This invention relates to novel amide derivatives of an amythiamicin which exhibit an antibacterial activity. This invention also relates to a pharmaceutical composition, especially an antibacterial composition, which comprises the novel amide derivative of an amythiamicin as an active ingredient.

BACKGROUND OF THE INVENTION

Amythiamicins A, B, C and D are antibacterially active antibiotics which are known and produced by cultivation of a microorganism, MI481-42F4 strain belonging to the genus Amycolatopsis and which are in the form of a cyclic peptide and all are hardly soluble in water. Amythiamicins A, B, C and D are described in the "Journal of Antibiotics" Vol 47, No. 6, pp. 668–674 (1994); ditto Vol 47, No. 10, pp. 1145–1159 (1994); and ditto Vol. 48, No. 2, pp. 182–184 (1995). The chemical structures of these amythiamicins are disclosed in the "Journal of Antibitotics" Vol. 47, No. 10, pp. 1153–1159 (1994). The amythiamicin-producing MI481-42F4 strain has such microbiological properties as described in the "Journal of Antibiotics" Vol. 47, No. 6, pp. 668–674 (1994) and was deposited in the "Fermentation Research Institute" under a deposit number of FERM P-12739 in February, 1992 and has now been deposited in the "National Institute of Bio-Science and Human-Technology, Agency of Industrial Science and Technology" at Tsukuba-shi, Ibaraki-ken, Japan, under a deposit number of FERM BP-6023 since Jul. 14, 1997 in terms of the Budapest Treaty.

Amythiamicin A is given under a name of Antibiotic MI481-42F4-A in Japanese Patent Application First Publication Kokai Hei 5-310766. Also Japanese Patent Application First Publication Kokai Hei 6-263784 describes antibacterial substances MI481-42F4-A1, -A2 and -A3 or their salts as such antibacterially active substances which are obtained by decomposing the MI481-42F4-A substance in dilute hydrochloric acid, or others. Further, Japanese Patent Application First Publication Kokai Hei 7-215989 describes antibacterial substances MI481-42F4-B1, -B2 and -B3 as such antibacterially active substances which are obtained by decomposing the MI481-42F4-A substance, for example, by methanolysis, etc., followed, if desired, by esterifying the resulting product. The MI481-42F4-A3 substance corresponds to amythiamicin B, MI481-42F4-A1 substance corresponds to amythiamicin C, MI481-42F4-B1 substance corresponds to amythiamicin D, and MI481-42F4-B2 substance corresponds to amythiamicin E, respectively.

Amythiamicins A to E are all the cyclic peptides which are hardly soluble in water. They possess antibacterial activities and are generally named as "amythiamicins". Amythiamicins are expected to be useful as antibacterial agent for medical purposes, particularly to be an antibacterial agent effective against methicillin-resistant *Staphylococcus aureus* (MRSA). However, amythiamicins are difficult to be formulated in the form of antibacterial compositions which can contain them in their antibacterially effective concentrations, because they are hardly soluble in water. That is to say, amythiamicins possess excellent antibacterial activities against gram-positive bacteria, particularly highly resistant MRSA, but amythiamicins are substantially insoluble in water, and hence they are very much limited in their methods of administrations when they are to be used as antimicrobial agents.

DETAILED DESCRIPTION OF THE INVENTION

In view of the above-mentioned circumstances, there exists an outstanding demand to prepare such new amythiamicin derivatives which are soluble in water and stable in aqueous solutions but can retain the original good antibacterial activities of the amytiamicins.

We, the present inventors, have eagerly made investigation in order to meet the outstanding demand. Thus, we have synthesized a variety of derivatives from the amythiamicins.

Amythiamicin D was obtained by methanolysis of amythiamicin A in the presence of hydrochloric acid and is a substance having the following formula:

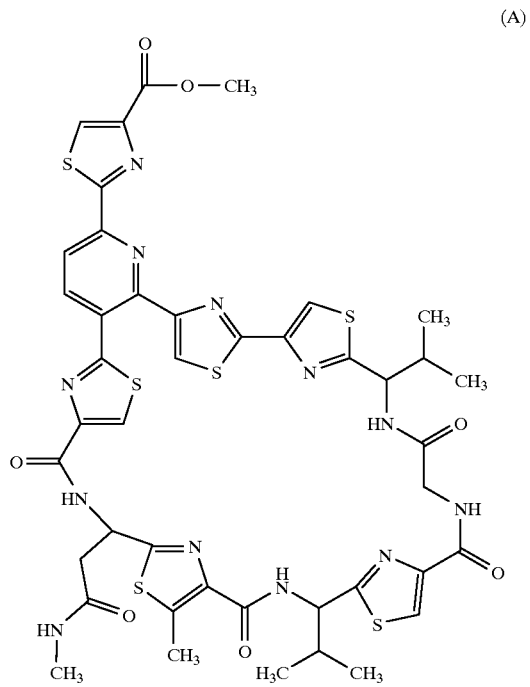

(A)

(see the "Journal of Antibiotics", Vol. 47, No. 10, pp. 1153–1159 (1994) referred to above).

We have now found that when amythiamicin D is saponified under mild reaction conditions in a usual manner, there is produced amythiamicin D acid (a free acid form) having the following formula

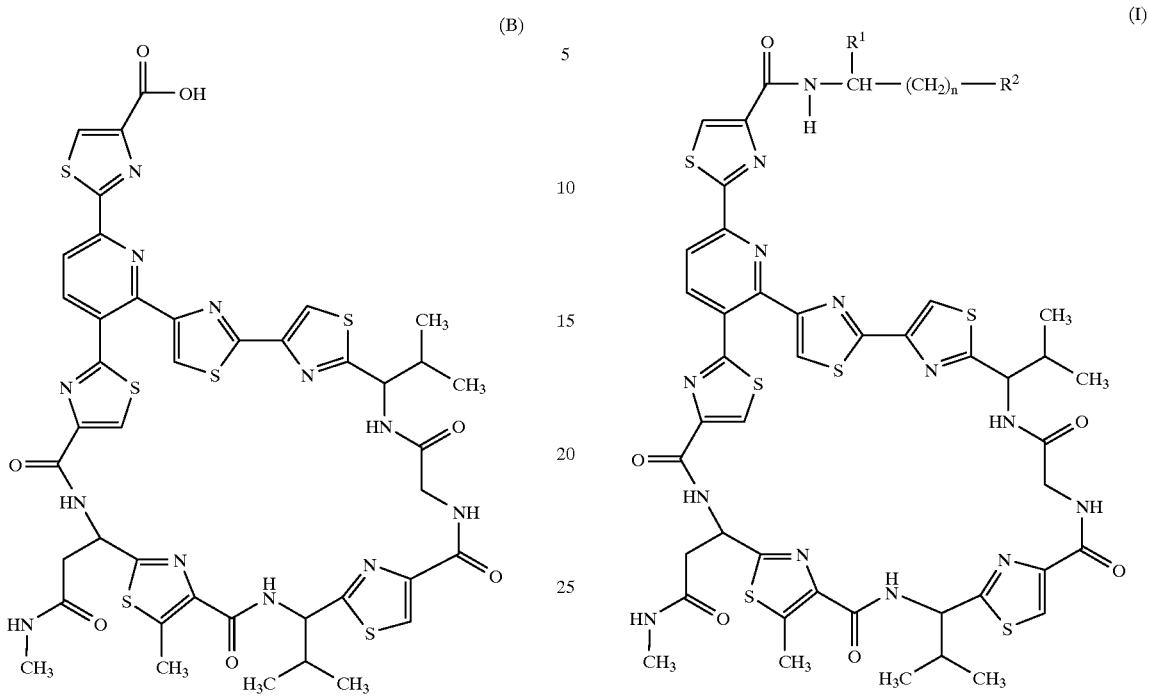

We have now further found that when the free carboxyl group at the 41-position of amythiamicin D acid of the above formula (B) is condensed with an amine derivative of the general formula (II)

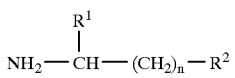

where n is an integer of 1–6, $R^1$ and $R^2$ have the meanings as defined hereinafter, in the presence of a condensation agent which may usually be used for the formation of a peptide linkage, there can be synthesized a variety of such new amide derivatives of the amythiamicin D acid which can be represented collectively by a general formula (I) given hereinafter, and further that these new amide derivatives of amythiamicin D acid now synthesized and the salts thereof are soluble in water and also are able to possess excellent antibacterial activities against gram-positive bacteria, particularly methicillin-resistant *Staphylococcus aureus* (MRSA). This invention has now been accomplished on the basis of these findings as above mentioned.

According to a first aspect of this invention, therefore, there is provided an amide derivative of an amythiamicin represented by the following general formula (I)

wherein n is an integer of 1 to 6, $R^1$ is a hydrogen atom, a carboxyl group or a hydroxylmethyl group, and $R^2$ is a group of the formula —$COOR^3$ where $R^3$ is a hydrogen atom or a lower alkyl group or a benzyl group of which phenyl ring may optionally be substituted by a halogen or a hydroxyl group, or $R^2$ is a group of the formula —$NR^4R^5$ where $R^4$ is a hydrogen atom or a lower alkyl group and $R^5$ is a hydrogen atom, a lower alkyl group, 3-aminopropyl group, 3-[2-(p-chloro or bromophenyl)ethyl]aminopropyl group or 3-(n-butylamino)propyl group, or $R^2$ is a methyl group, a hydroxyl group or a guanidino group of the formula —NH—C(=NH)—$NH_2$, or a pharmaceutically acceptable salt or ester thereof.

In the derivative of the above general formula (I), n is preferably an integer of 2–5. When $R^3$, $R^4$ or $R^5$ in the formula (I) is a lower alkyl group, the lower alkyl group may contain 1–6 carbon atoms, preferably 1–4 carbon atoms and may be of straight or branched chain. Preferred examples of the lower alkyl groups include methyl, ethyl, n-propyl, isopropyl, n-butyl, isobutyl, n-pentyl and n-hexyl groups.

Pharmaceutically acceptable salts of the amythiamicin amide derivative of the general formula (I) may be sodium salt, potassium salt, calcium salt and magnesium salt if at least one carboxyl group is present in said derivative. In cases where said derivative contains an amino group and/or an imino group, the salts may also be in the form of acid addition salts with a pharmaceutically acceptable inorganic or organic acid, such as hydrochloric acid, sulfuric acid, acetic acid, propionic acid and methanesulfonic acid.

If the amythiamicin amide derivative of the general formula (I) contains one or two, free carboxyl group(s), it may form a pharmaceutically acceptable ester with a pharmaceutically acceptable ester-forming group which may be, for example, a lower alkyl group (e.g., methyl and ethyl groups) and a benzyl group.

The amythiamicin amide derivative of the general formula (I) according to the first aspect of this invention embraces the following four classes of said derivative:

(1) A compound of the formula (Ia)

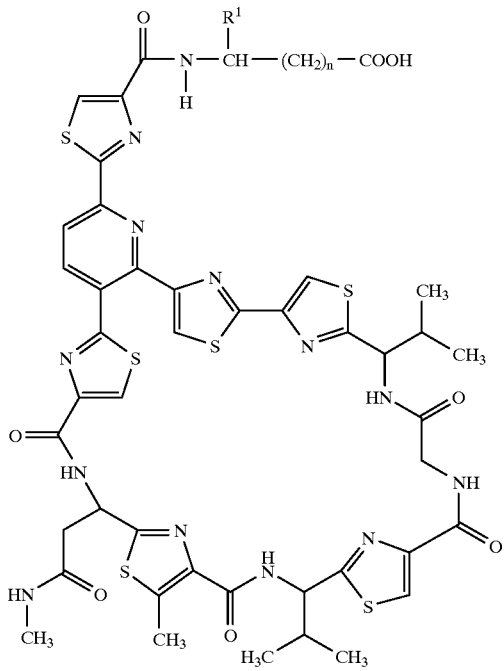

(Ia)

wherein n is an integer of 1 to 6 and $R^1$ is a hydrogen atom, a carboxyl group or a hydroxymethyl group, or a pharmaceutically acceptable salt thereof or a lower alkyl ester or a benzyl ester thereof.

(2) A compound of the formula (Ib)

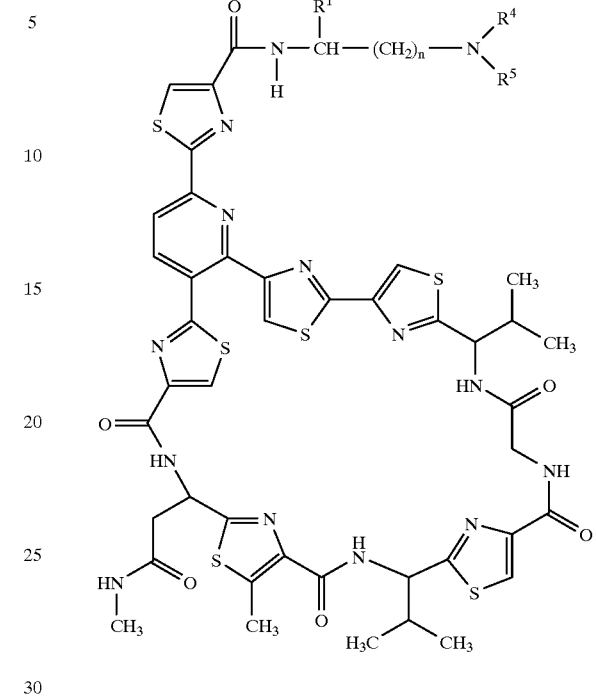

(Ib)

wherein n is an integer of 1 to 6, $R^1$ is a hydrogen atom, a carboxyl group or a hydroxymethyl group, and $R^4$ is a hydrogen atom or a lower alkyl group and $R^5$ is a hydrogen atom, a lower alkyl group, 3-amino-propyl group, 3-[2-(p-chloro or bromo-phenyl)ethyl]aminopropyl group or 3-(n-butylamino)propyl group, or a pharmaceutically acceptable salt therof or a lower alkyl ester or a benzyl ester thereof.

(3) A compound of the formula (Ic)

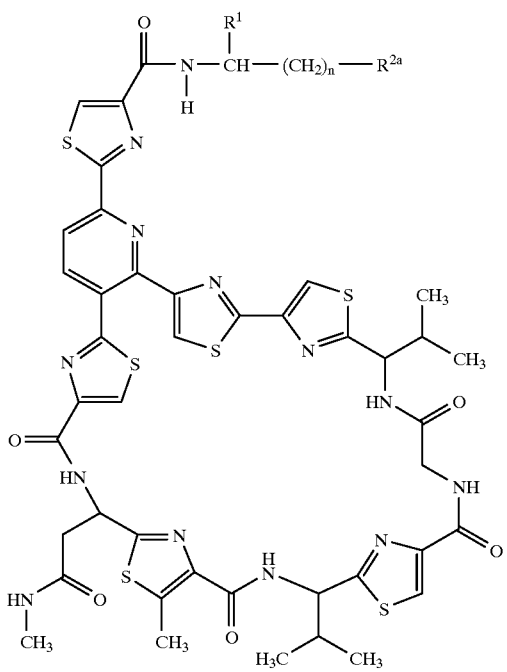

wherein n is an integer of 1 to 6, $R^1$ is a hydrogen atom, a carboxyl group or a hydroxymethyl group and $R^{2a}$ is a methyl group or a hydroxyl group, or a pharmaceutically acceptable salt thereof or a lower alkyl ester or a benzyl ester thereof.

(4) A compound of the formula (Id)

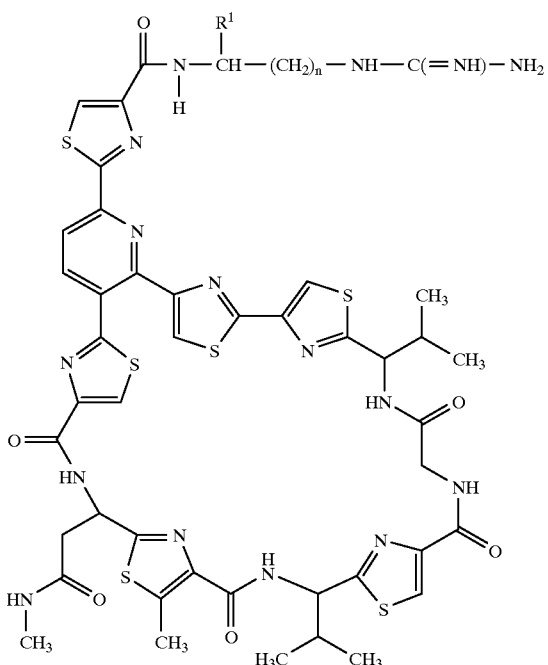

wherein n is an integer of 1 to 6, and $R^1$ is a hydrogen atom, a carboxyl group or a hydroxymethyl group, or a pharmaceutically acceptable salt or a lower alkyl ester or a benzyl ester thereof.

The preparation of the amythiamicin amide derivatives of the general formula (I) according to the first aspect of this invention may be effected by condensing amythiamicin D acid of the formula (B) with an amine derivative of the general formula (II)

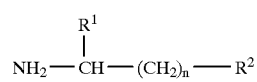

where n, $R^1$ and $R^2$ have the meanings as defined in the general formula (I), or a protected derivative of the amine derivative of the formula (II), with forming an amido-linkage. Said protected derivative may be used when the amine derivative of the formula (II) itself has a functional group such as carboxyl group, amino group or guanidino group, and the protecting group for such functional group may properly be selected. For example, t-butoxycarbonyl group as an amino-protecting group and diphenylmethyl group as a carboxyl-protecting ester group are preferably selected.

Particular examples of the amine derivative of the above formula (II) include methyl 6-aminocaproate, bis(3-aminopropyl)methylamine, trimethylene diamine, 3-(3-aminopropylamino)propyl-n-butylamine, N-(3-aminopropyl)-N-{3-[2-(p-chlorophenyl)ethylamino]propyl}-methylamine, n-butylamine, 3-hydroxypropylamine, N',N"-bis(t-butoxycarbonyl)-L-arginine diphenylmethyl ester and N',N"-bis-(t-butoxycarbonyl)-L-arginol.

The condensation reaction may preferably be carried out in the presence of a condensation agent which is used conventionally for the synthesis of peptides. If necessary, the protecting group which may be present in the resulting condensation product is removed therefrom by subjecting the product to such a deprotecting reaction which is usually employed in the chemistry of peptides. Also, if desired, the resulting condensation product may further be subjected to such modification reactions as saponification, acylation, alkylation and the like.

As the condensation agent to be used for the formation of the amide linkage in the above-mentioned condensation reaction, there may be used a conventional condensation agent which is used in the chemistry of peptide synthesis and may be, for example, carbodiimides such as DDC, EDC, etc.; phosphate derivatives such as DPPA, DEPC, etc.; phosphonium salts such as Bop reagent, PyBop reagent, etc.; uronium salts such as TBTU, HBTU, TNTU and the like, as well as any of those reagents in combination with HOBt, HOSu and the like. For the solvent for effecting the condensation reaction, there may be used any of those organic solvent which are capable of dissolving both the condensation agent and the amythiamicin D acid and are conventionally used for the synthesis of peptides. Preferred organic solvents may include aprotic polar solvents such as DMF, N-methylpyrrolidone and the like. Suitably, a reaction temperature of 0° C.–70° C. and a reaction time of 1–48 hours may be chosen.

The condensation product so obtained may be isolated by one or any combination of conventional methods such as gel filtration chromatography, silica gel chromatography, reversed phase chromatography and others, with monitoring the ultraviolet absorption spectrum of the product. When the resulting reaction product contains any remaining protective group, the removal of the protective group is effected by the deprotecting reaction conventionally used for the peptide chemistry, followed by the isolation and purification of the desired reaction product with using the above-mentioned purification method(s).

Some preferred examples of the amide derivative of the general formula (I) according to this invention are listed in Table 1 below, with reference to their compound numbers, wherein Compound No. 1 to No. 11 are produced in Examples 1–11 given hereinafter to illustrate the production of these compounds according to this invention.

Compounds Nos. 1 to 3 shown in Table 1 are included by the compound of the formula (Ia) given hereinbefore. Among them, most preferred is a compound of the formula (Ia-1)

TABLE 1

General formula (I)

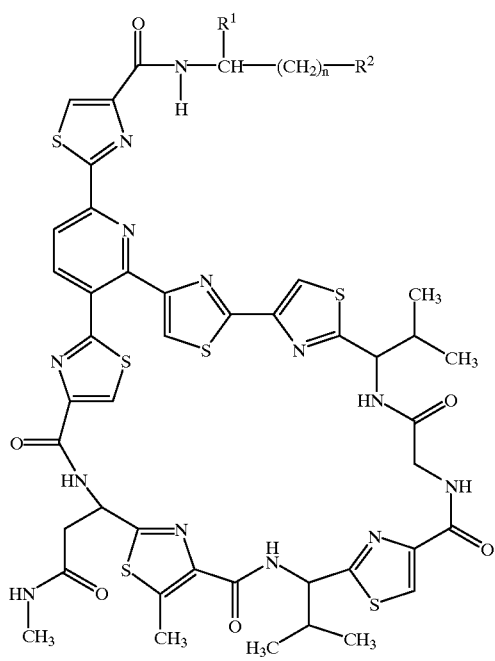

(I)

| Compound No. of this invention (Example No. for illustrative production thereof) | Formula (I) | | |
|---|---|---|---|
| | $R^1$ | n | $R^2$ |
| 1 | H | 4 | —COOCH$_3$ |
| 2 | H | 4 | —COOH |
| 3 | H | 4 | —COONa |
| 4 | H | 2 | —N(CH$_3$)—(CH$_2$)$_3$—NH$_2$ |
| 5 | H | 2 | —NH$_2$ |
| 6 | H | 2 | —NH—(CH$_2$)$_3$—NH—C$_4$H$_9$ |
| 7 | H | 2 | 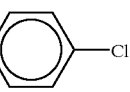 |
| 8 | H | 2 | —CH$_3$ |
| 9 | H | 2 | —OH |
| 10 | —COOH | 3 | —NH—C(=NH)—NH$_2$ |
| 11 | —CH$_2$OH | 3 | —NH—C(=NH)—NH$_2$ |

(Ia-1)

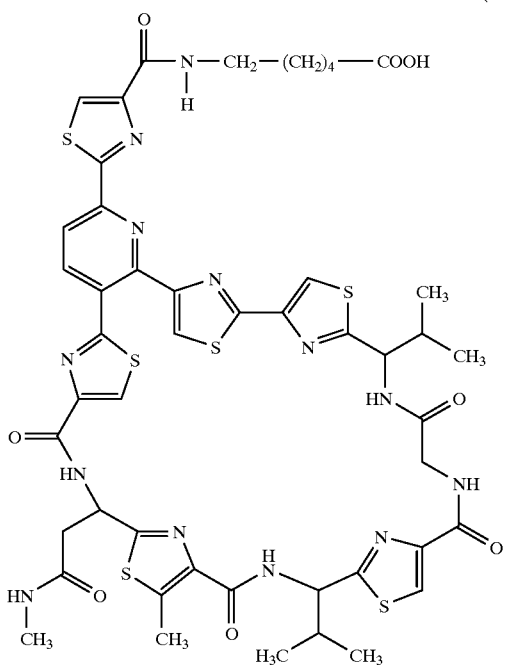

or a pharmaceutically acceptable salt thereof or a lower alkyl ester or a benzyl ester thereof.

Compounds Nos. 4 to 7 shown in Table 1 are included by the compound of the formula (Ib) given hereinbefore. Among them, most preferred is a compound of the formula (Ib-1)

(Ib-1)

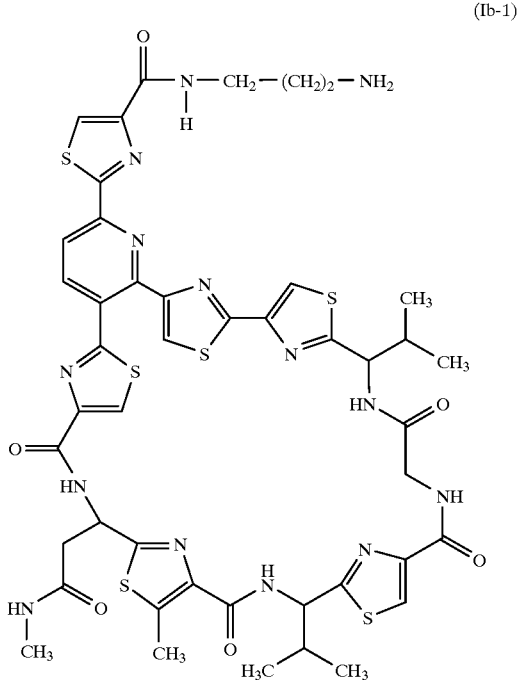

or a pharmaceutically acceptable salt thereof.

Compounds Nos. 8 and 9 shown in Table 1 are included by the compound of the formula (Ic) above.

Among them, preferred is a compound of the formula (Ic-1)

(Ic-1)

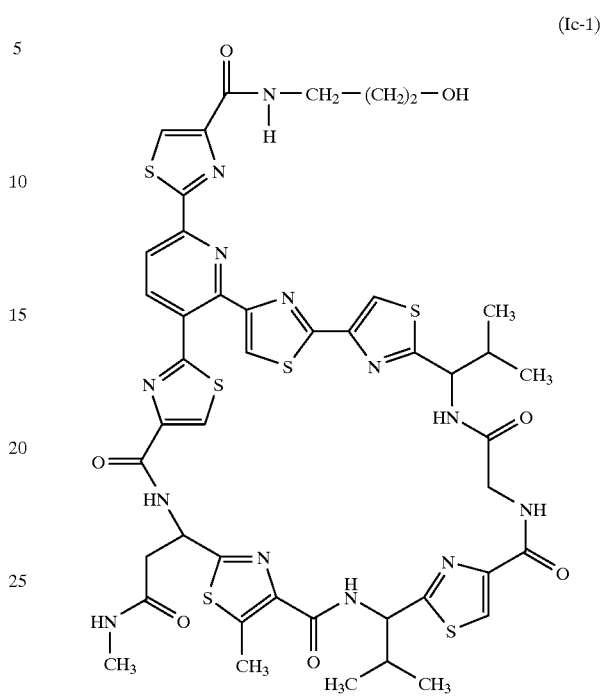

Compounds Nos. 10 and 11 shown in Table 1 are included by the compound of the formula (Id) given hereinbefore.

The antibacterial activities of the amythiamicin amide derivative of the general formula (I) according to this invention are now concretely described. Compounds No. 1 to No. 11 according to this invention, which were respectively prepared in Examples 1 to 11 hereinafter given, were tested as the test compounds for their minimum inhibitory concentrations (MIC.) ($\mu$g/ml) against growth of a variety of test microorganisms by a standard serial dilution method. In the tests, the incubation medium used was Müller-Hinton agar medium and the incubation temperature was 37° C. The test results are shown as antibacterial spectra in the following Tables 2 and 3.

TABLE 2

| | Minimum growth inhibitory concentrations (MIC.) ($\mu$g/ml) Compound No. | | | | | |
|---|---|---|---|---|---|---|
| Test microorganisms | 1 | 2 | 4 | 5 | 6 | 7 |
| Staphylococcus aureus FDA 209P | 50 | 0.1 | 12.5 | 0.78 | 50 | >100 |
| Staphylococcus aureus Smith | >100 | 0.1 | 12.5 | 3.12 | 25 | >100 |
| Staphylococcus aureus MS 9610 | >100 | 0.2 | 50 | 3.12 | >100 | >100 |
| Staphylococcus aureus No. 5 (MRSA) | >100 | 0.2 | >100 | 6.25 | >100 | >100 |
| Staphylococcus aureus No. 17 (MRSA) | >100 | 0.2 | >100 | 6.25 | >100 | >100 |
| Staphylococcus aureus MS 16526 | >100 | 0.2 | >100 | 6.25 | >100 | >100 |
| Staphylococcus aureus TY-0428 | >100 | 0.2 | >100 | 3.12 | >100 | >100 |
| Micrococcus luteus FDA 16 | >100 | 0.39 | >100 | 12.5 | >100 | 6.25 |
| Micrococcus luteus IFO 3333 | >100 | 0.39 | >100 | 3.12 | >100 | 12.5 |
| Micrococcus luteus PIC 1001 | 3.13 | 0.1 | 3.12 | 0.78 | >100 | 12.5 |
| Bacillus anthracis | 0.98 | <0.03 | 3.12 | 0.78 | 25 | >100 |

TABLE 2-continued

| Test microorganisms | Minimum growth inhibitory concentrations (MIC.) (μg/ml) Compound No. | | | | | |
|---|---|---|---|---|---|---|
| | 1 | 2 | 4 | 5 | 6 | 7 |
| Bacillus subtilis NRRL B-558 | >100 | 1.56 | >100 | 6.25 | 25 | >100 |
| Bacillus subtilis PCI 219 | >100 | 0.2 | >100 | 3.12 | >100 | 50 |
| Bacillus cereus ATCC 10702 | 3.13 | 0.1 | 6.25 | 1.56 | >100 | >100 |
| Corynebacterium bovis 1810 | >100 | 0.31 | >100 | >100 | >100 | 25 |
| Escherichia coli NIHJ | >100 | >100 | >100 | >100 | >100 | >100 |
| Escherichia coli K-12 | >100 | >100 | >100 | >100 | >100 | >100 |
| Escherichia coli K-12 ML 1692 | >100 | >100 | >100 | >100 | >100 | >100 |
| Escherichia coli BEM 11 | >100 | >100 | >100 | >100 | >100 | >100 |
| Escherichia coli BEM 1121 | >100 | >100 | >100 | >100 | >100 | >100 |
| Escherichia coli BE 1186 | >100 | >100 | >100 | >100 | >100 | >100 |
| Shigella dysenteria JS 11910 | >100 | 3.13 | >100 | >100 | >100 | >100 |
| Shigella clexnerl JS 11749 | >100 | >100 | >100 | >100 | >100 | >100 |
| Shigella sonnei JS 11746 | >100 | >100 | >100 | >100 | >100 | >100 |
| Salmonella typhi T-63 | >100 | >100 | >100 | >100 | >100 | >100 |
| Salmonella enteritidis 1891 | >100 | 6.25 | >100 | >100 | >100 | >100 |
| Proteus vulgaris OX 19 | >100 | >100 | >100 | >100 | >100 | >100 |
| Proteus mirabilis IFM OM-9 | >100 | >100 | >100 | >100 | >100 | >100 |
| Providencia rettgeri GN 311 | >100 | >100 | >100 | >100 | >100 | >100 |
| Providencia rettgeri GN 466 | >100 | >100 | >100 | >100 | >100 | >100 |
| Serratia marcescens | >100 | >100 | >100 | >100 | >100 | >100 |
| Pseudomonas aeruginosa A3 | >50 | >50 | >100 | >100 | >100 | >100 |
| Pseudomonas aeruginosa GN315 | >100 | >100 | >100 | >100 | >100 | >100 |
| Klebsiella pneumonia PCI 602 | >100 | >100 | >100 | >100 | >100 | >100 |
| Mycobacterium smegmatis ATCC 607 | ND | ND | >100 | >100 | >100 | >100 |
| Candida albicans 3147 | >100 | >100 | >100 | >100 | >100 | >100 |

Note: "ND" means "not determined".

TABLE 3

| Test microorganisms | Minimum growth inhibitory concentrations (MIC.) (μg/ml) Compound No. | | | |
|---|---|---|---|---|
| | 8 | 9 | 10 | 11 |
| Staphylococcus aureus 209P JC-1 | >100 | 0.39 | >100 | 6.25 |
| Staphylococcus aureus M 133 | >100 | 0.39 | >100 | >100 |
| Staphylococcus aureus M 126 | >100 | 0.39 | >100 | >100 |
| Staphylococcus aureus MS 15009/pMS 99 | >100 | 0.39 | >100 | >100 |
| Staphylococcus aureus MS 15026 | >100 | 0.39 | >100 | >100 |
| Staphylococcus aureus MS 15009/pMS 98 | >100 | 0.39 | >100 | >100 |
| Staphylococcus aureus MS 15027 | >100 | 0.39 | >100 | >100 |
| Staphylococcus epidermidis ATCC 14990 | >100 | 0.78 | >100 | >100 |
| Micrococcus luteus ATCC 9341 | 1.56 | 0.20 | >100 | 100 |
| Enterobacterium faecalis W-73 | >100 | 0.39 | >100 | >100 |
| Escherichia coli NIHJ JC-2 | >100 | >100 | >100 | >100 |
| Klebsiella pneumonia PCI 602 | >100 | >100 | >100 | >100 |
| Streptococcus pneumoniae IP 692 | >100 | >100 | >100 | >100 |
| Streptococcus pneumoniae Type 1 | >100 | >100 | >100 | >100 |
| Streptococcus pyogenes Cook | >100 | >100 | >100 | >100 |
| Branhamella catarrhalis W-0500 | >100 | >100 | >100 | >100 |
| Branhamella catarrhalis W-0506 | >100 | >100 | >100 | >100 |
| Haemophilus influenzae 9334 | >100 | >100 | >100 | >100 |
| Haemophilus influenzae Type b | >100 | >100 | >100 | >100 |

Thus, it is evident that the amythiamicin amide derivative of the formula (I) according to the first aspect of this invention is antibacterially active against a variety of gram-positive bacteria and is of a pharmaceutical utility.

In a second aspect of this invention, therefore, there is provided a pharmaceutical composition which comprises an amount of the amide derivative of amythiamicin having the formula (I) as defined above or a salt or an ester thereof as an active ingredient, in association with a pharmaceutically acceptable carrier for the active ingredient. This pharmaceutical composition may be an antibacterial composition comprising an antibacterially effective amount of the amide derivative of amythiamicin having the formula (I) as defined above or a salt or an ester thereof.

The pharmaceutically acceptable carrier which may be incorporated in the composition of the second aspect of this invention may be either a solid carrier such as starch, sucrose and other conventional ones, or a liquid carrier such as water, physiological saline, ethanol and other conventional ones.

The pharmaceutical composition according to the second aspect of this invention may be formulated into an orally administrable preparation such as a powder, tablets, capsules, and solutions, in a manner known in the art of pharmaceutics. This pharmaceutical composition may also be formulated into an intravenously or intraperitoneally administrable preparation such as injectable solutions, in a manner known in the art of pharmaceutics.

In a third aspect of this invention, there is provided a method for the manufacture of a phamaceutical composition, particuarly an antibacterial composition, which comprises mixing an amide derivative of amythiamicin having the formula (I) or a salt or an ester thereof with a pharmaceutically acceptable solid or liquid carrier.

In a further aspect of this invention, there is provided use of an amide derivative of amythiamicin having the formula (I) or a salt or an ester thereof in the manufacture of a pharmaceutical composition.

The production of typical examples of the new compounds according to this invention is now illustrated with reference to the following Examples to which this invention is not limited.

EXAMPLE 1

Amythiamicin D acid (22.6 mg), methyl 6-amino-caproate hydrochloride (13.4 mg), Bop reagent (31.6 mg) and HOBt (10 mg) were dissolved in N-methylpyrrolidone (0.25 ml). After triethylamine (0.012 ml) was added, the resulting solution was stirred at room temperature for 21 hours to conduct the condensation reaction intended. To the resulting reaction solution was added methanol (2 ml), and the mixture so obtained was poured into a column of Sephadex LH20 which had been packed with aid of methanol. Through the column, methanol was then passed as an eluent for the development. Fractions of the eluate so developed which showed the presence of the chromophoric group of amythiamicin were collected with monitoring the ultraviolet absorption peaks of each fraction. The solvent used was evaporated under a reduced pressure from the fractions so collected, whereby a crude product of the target compound (54.1 mg) was obtained.

The crude product was dissolved in chloroform (1 ml) and the resulting solution was poured into a column of silica gel (Wako-gel C300) (12 ml) which had been packed with aid of chloroform. The silica gel column was then developed successively with chloroform, chloroform containing 2% methanol, chloroform containing 5% methanol, and chloroform containing 6% methanol. The target compound was eluted in the fractions of the eluate which were developed with the 5% methanol-containing chloroform and with the 6% methanol-containing chloroform. The solvent used was evaporated from the collected fractions under a reduced pressure to yield Compound No. 1 (23.4 mg) which is shown in Table 1 and was in the form of a methyl ester.

Mass spectrum (FAB-): 1143.2, 1142.2, 459.2, 458.1 (FAB+): 1144.2, 1143.2

Ultraviolet absorption spectrum: Same as that of amythiamicin A

EXAMPLE 2

Compound No. 1 (14 mg) as obtained in Example 1 above was dissolved in chloroform (0.5 ml), and to the resulting solution were added methanol (1.5 ml) and then a 1N aqueous NaOH solution (0.6 ml). The resulting mixture was stirred at room temperature for 90 minutes to effect the reaction intended. The progress of the hydrolysis reaction could be monitored by a thin layer chromatography (silica gel, developed with chloroform-methanol, 10:1, while the target compound spot was detected by ultraviolet lamp irradiation).

After the completion of the reaction, the resulting reaction solution was neutralized with a 1N hydrochloric acid (0.6 ml) and then concentrated. The concentrated solution was poured into a column of Sephadex LH20 which was packed with aid of methanol. This column was then eluted with methanol. Fractions of the eluate which showed the presence of the chromophoric group of amythiamicin were collected with monitoring the ultraviolet absorption of each fraction. The solvent was evaporated from the collected fractions under a reduced pressure to yield Compound No. 2 (8.3 mg) which is shown in Table 1 and was in the form of the free carboxylic acid.

Mass spectrum (FAB-): 1129.1, 1128.1 (AFB+): 1131.3, 1130.3

Ultraviolet absorption spectrum: Same as that of amythiamicin A

EXAMPLE 3

Compound No. 2 (4.1 mg) as obtained in Example 2 above was dissolved in methanol (1 ml) and a 0.1N aqueous NaOH solution (0.036 ml) was added thereto. The resulting solution was evaporated to dryness under a reduced pressure to give the sodium salt of Compound No. 2. This sodium salt (Compound No. 3 shown in Table 1) gave a clear and easily foamable aqueous solution when 4 mg of the sodium salt was dissolved in water (0.4 ml).

EXAMPLE 4

Amythiamicin D acid (10.3 mg), 0.034 ml of a solution of bis(3-aminopropyl)methylamine (0.2 ml) in N-methylpyrrolidone (0.6 ml), Bop reagent (14.8 mg) and HOBt (9.4 mg) were dissolved in N-methylpyrrolidone (0.09 ml). To the resulting solution was added triethylamine (0.012 ml), and the mixture so obtained was stirred at room temperature for 19 hours to effect the reaction intended. After addition of methanol (2 ml), the resulting reaction solution was poured into a column of Sephadex LH20 which was packed with aid of methanol, and the column was eluted with methanol. Fractions of the eluate which showed the presence of the chromophoric group of amythiamicin were collected with monitoring the ultraviolet absorption of each fraction. The solvent was evaporated from the collected fractions under a reduced pressure, to give a crude product of the target compound (11.2 mg). The crude product was again purified by chromatography on Sephadex LH20 with monitoring the ultraviolet absorption so that there were obtained such eluate fractions containing the intended compound. The solvent was evaporated from the collected fractions under a reduced pressure to afford Compound No. 4 (8.6 mg) which is shown in Table 1.

Mass spectrum (FAB+): 1145.2, 1144.2, 1087.2 (M—(NH$_2$—(CH$_2$)$_3$—))

Ultraviolet absorption spectrum: Same as that of amythiamicin A

EXAMPLE 5

Amythiamicin D acid (11.2 mg), 0.012 ml of a solution of trimethylene diamine (0.2 ml) in N-methylpyrrolidone (0.5 ml), Bop reagent (14.7 mg) and HOBt (5.4 mg) were dissolved in N-methylpyrrolidone (0.06 ml). To the resulting solution was added triethylamine (0.0025 ml), and the mixture so obtained was stirred at room temperature for 20 hours to effect the reaction intended. To the resulting reaction solution were added methanol (0.2 ml) and then methanol containing 10% hydrogen chloride (20 drops). The resulting solution was poured into a column of Sephadex LH20 which was packed with aid of methanol, and the column was eluted with methanol. Fractions of the eluate which showed the presence of the chromophoric group of amythiamicin were collected with monitoring the ultraviolet absorption of each fraction.

The solvent was evaporated from the so collected fractions under a reduced pressure and the residue obtained was dissolved in a 50% aqueous methanol and the methanolic solution was adsorbed on a small column of ODS-silica (3 ml) which was packed with aid of a 50% aqueous methanol. The column was then washed with a 50% aqueous methanol and then eluted with methanol. The fractions of the eluate containing the target compound were collected with monitoring the ultraviolet absorption of each fraction. The solvent was evaporated from the so collected fractions under a reduced pressure to afford Compound No. 5 (8.6 mg) which is shown in Table 1.

Mass spectrum (FAB+): 1074.3, 1073.3

Ultraviolet absorption spectrum: Same as that of amythiamicin A

EXAMPLE 6

Amythiamicin D acid (10.6 mg), 3-(3-aminopropyl-amino)propyl-n-butylamine trihydrochloride (9.9 mg), Bop reagent (13.9 mg) and HOBt (5.2 mg) were dissolved in N-methylpyrrolidone (0.13 ml). After triethylamine (0.015 ml) was added thereto, the resulting solution was stirred at room temperature for 20 hours to conduct the condensation reaction intended. To the resulting reaction solution were added methanol (0.3 ml) and a 10% hydrogen chloride-containing methanol (0.2 ml), and the mixture so obtained was poured into a column of Sephadex LH20 which was packed with aid of methanol. Then, the column was eluted with methanol. Fractions of the eluate which showed the presence of the chromophoric group of amythiamicin were collected together with monitoring the ultraviolet absorption of each fraction.

The solvent was evaporated from the collected fractions under a reduced pressure to give a crude product of the target compound (26.2 mg). This crude product was dissolved in a 50% aqueous methanol and the methanolic solution was adsorbed on a small column of ODS-silica (3 ml) packed with aid of a 50% aqueous methanol. The ODS-silica column was then washed with a 50% aqueous methanol and then eluted with methanol. Fractions of the eluate which contained the target compound were collected with monitoring the ultraviolet absorption of each fraction. The solvent was evaporated from the collected fractions under a reduced pressure to afford Compound No. 6 (7.0 mg) which is shown in Table 1.

Mass spectrum (FAB+): 1187.4, 1186.4

Ultraviolet absorption spectrum: Same as that of amythiamicin A

EXAMPLE 7

Amythiamicin D acid (11.5 mg), N-(3-aminopropyl)-N-{3-[2-(p-chlorophenyl) ethylamino]propyl}-methylamine trihydrochloride (14.1 mg), Bop reagent (16.0 mg) and HOBt (6.1 mg) was dissolved in N-methylpyrrolidone (0.23 ml). The resulting solution, after addition of triethylamine (0.015 ml) thereto, was stirred at room temperature for 19.5 hours to effect the condensation reaction. Thereafter, methanol (0.3 ml) was added to the resalting reaction solution, which was then poured into a column of Sephadex LH20 which was packed with aid of methanol. Then, the elution was effected with methanol. Fractions of the eluate which showed the presence of the chromophoric group of amythiamicin were collected with monitoring the ultraviolet absorption of each fraction.

The solvent was evaporated from the so collected fractions under a reduced pressure and the residue obtained was dissolved in a 50% aqueous methanol. The methanolic solution obtained was adsorbed on a small column of ODS-silica (1.8 ml) packed with aid of a 50% methanol. The column was then washed with a 50% aqueous methanol and then eluted with a 10% acetic acid-containing methanol. Fractions of the eluate which contained the target compound were collected with monitoring the ultraviolet absorption of each fraction. The solvent used was evaporated from the collected fractions under a reduced pressure to afford Compound No. 7 (9.6 mg) which is shown in Table 1.

Mass spectrum (FAB+): 1284.4, 1282.4

Ultraviolet absorption spectrum: Same as that of amythiamicin A

EXAMPLE 8

Amythiamicin D acid (20 mg) and HOBt (13 mg) were dissolved in N,N-dimethylformamide (3 ml), to which was then added 1-ethyl-3-(3'-dimethylaminopropyl) carbodiimide hydrochloride (as a condensing agent) (16.4 mg), and the resultant mixture was stirred at room temperature for 30 minutes. Then, N-butylamine (12.4 mg) as a reactant was added thereto and the reaction mixture so obtained was stirred at room temperature for 3 hours to effect the reaction intended.

The resulting reaction solution was diluted with chloroform (5 ml) and the diluted solution was washed with water and dried over anhydrous sodium sulfate. The solvent was evaporated from said solution under a reduced pressure to give a crude product of the target compound, which was then dissolved in chloroform (1 ml). The chloroform solution was poured into a column of a silica gel (Wako-gel C200) (10 ml) which was packed with aid of a 6.6% methanol-containing chloroform. The silica gel column was then eluted with a 3.3% methanol-containing chloroform. Such fractions of the eluate which showed the presence of the chromophoric group of amythiamicin were collected with monitoring the ultraviolet absorption of each fraction. The solvent was evaporated from the collected fraction under a reduced pressure to afford Compound No. 8 (19.5 mg) which is shown in Table 1.

Mass spectrum (FD):1072 (M+)

Ultraviolet absorption spectrum: Same as that of amythiamicin A

EXAMPLE 9

Amythiamicin D acid (29.8 mg) and HOBt (22.4 mg) were dissolved in N,N-dimethylformamide (5 ml), to which was then added 1-ethyl-3-(3'-dimethylaminopropyl) carbodiimide hydrochloride (as a condensing agent) (28.4 mg). The resultant mixture was stirred at room temperature for 30 minutes. Then, 3-hydroxypropylamine (4.4 mg) as a reactant was added thereto and the mixture so obtained was stirred at room temperature for 2 hours to effect the reaction intended.

The resulting reaction solution was diluted with methylene chloride (10 ml) and the diluted solution was washed with water and dried over anhydrous sodium sulfate. The solvent was evaporated from said solution under a reduced pressure to give a crude product of the target compound. The crude product was dissolved in chloroform (1 ml) and the chloroform solution was poured into a column of silica gel (Wako-gel C-300) (11 ml) which was packed with aid of a 3.3% methanol-containing chloroform. The column was eluted with a 3.3% methanol-containing chloroform. Such fractions of the eluate which showed the presence of the chromophoric group of amythiamicin were collected with monitoring the ultraviolet absorption of each fraction. The solvent was evaporated from the collected fractions under a reduced pressure, so that Compound No. 9 (14.6 mg) shown in Table 1 was obtained as the target compound.

Mass spectrum (FD):1074 (M+)

Ultraviolet absorption spectrum: Same as that of amythiamicin A

EXAMPLE 10

Amythiamicin D acid (50 mg) and HOBt (37.5 mg) were dissolved in N,N-dimethylformamide (8 ml), to which was then added 1-ethyl-3-(3'-dimethylaminopropyl) carbodiimide hydrochloride (48 mg) (as a condensation agent). The resultant mixture was stirred at room temperature for 30 minutes. Then, diphenylmethyl ester of N',N"-bis-(t-butoxycarbonyl)-L-arginine (53 mg) as a reactant was added thereto, and the mixture so obtained was stirred at room temperature for 3 hours to conduct the condensation reaction intended.

The resulting reaction solution was diluted with methylene chloride (20 ml), then washed with water and dried over anhydrous sodium sulfate. The solvent was then evaporated from the reaction solution under a reduced pressure to give a crude product of the intended compound. This crude product was dissolved in chloroform (1 ml) and the solution was poured into a Wako-gel C300 (6 ml) column which was packed with aid of a 3.3% methanol-containing chloroform. The column was eluted with a 3.3% methanol-contaning chloroform. Such fractions of the eluate which showed the presence of the chromophoric group of amythiamicin were collected with monitoring the ultraviolet absorption. The solvent was evaporated from the collected fractions under a reduced pressure, and there was thus obtained the condensation product intended (55.3 mg) which contained the t-butoxycarbonyl groups as the amino protecting group.

The condensation product obtained was dissolved in anisole (0.3 ml), to which was then added trifluoroacetic acid (0.7 ml) under ice-cooling. The resulting mixture was gradually warmed up to room temperature under stirring and was then maintained at room temperature under stirring for 2 hours, so that the deprotecting reaction intended was effected. Isopropylether (3 ml) was added to the reaction solution so obtained, and the precipitate as formed was filtered, washed with isopropylether and dried to afford Compound No. 10 (30.7 mg) shown in Table 1, as the target compound.

Mass spectrum (FD):1173 (M+)

Ultraviolet absorption spectrum: Same as that of amythiamicin A

EXAMPLE 11

Amythiamicin D acid (23 mg) and HOBt (17 mg) were dissolved in N,N-dimethylformamide (5 ml), to which solution was added 1-ethyl-3-(3'-dimethylaminopropyl)-carbodiimide hydrochloride (18 mg) (as a condensation agent). The resultant mixture was stirred at room temperature for 30 minutes. Then, N',N"-bis(t-butoxycarbonyl)-L-arginol (24 mg) as a reactant was added thereto, and the reaction mixture so obtained was further stirred at room temperature for 15 hours to conduct the condensation reaction intended.

The resulting reaction solution was diluted with chloroform (10 ml), washed with water and dried over anhydrous sodium sulfate. The solvent was evaporated from the dried solution under a reduced pressure to give a crude product of the intended compound, which was then dissolved in chloroform (1 ml). The resulting chloroform solution was poured into a Wako-gel C200 (6 ml) column which was packed with aid of a 5% methanol-containing chloroform. The column was then eluted with a 5% methanol-containing chloroform. Such fractions which showed the presence of the chromophoric group of amythiamicin were collected with monitoring the ultraviolet absorption of each fraction. The solvent was evaporated from the collected fractions under a reduced pressure to give the intended condensation product (15.4 mg).

The condensation product so obtained was dissolved in anisole (0.5 ml), to which was then added a methanolic solution (3 ml) of 5N hydrochloric acid under ice-cooling. The resultant mixture was gradually warmed up to room temperature under stirring and was maintained at that temperature for 2 hours under stirring, whereby the deprotecting reaction intended was effected. The reaction solution so obtained was concentrated under a reduced pressure, and a saturated aqueous sodium hydrogen carbonate was then added to the concentrated solution to cause precipitation. The precipitate as formed was recovered by filtration, washed with ethyl acetate and dried. Thus, Compound No. 11 (10 mg) which is shown in Table 1 was obtained as the target compound.

Mass spectrum (FD):1159 (M+)

Ultraviolet absorption spectrum: Same as that of amythiamicin A.

As described hereinbefore, the new amythiamicin amide derivative of the general formula (I) according to this invention is produced with using amythiamicin D acid of the formula (B) as a starting material. This amythiamicin D acid can be prepared from amythiamicin D of the formula (A) by cleaving the ester-forming methyl group from the methoxycarbonyl group at the 41-position of amythiamycin D through alkaline hydrolysis of amythiamicin D, followed by treatment of the hydrolysis product with a diluted hydrochloric acid. Amythiamicin D, in turn, can be produced by methanolysis of amythiamicin A. Incidentally, a fermentative production of amythiamicins A, B, C and D by cultivation of Amycolatopsis sp. MI148-42F4 is reported at pages 671–672 of the "Journal of Antibiotics" Vol. 47, No. 6 (1994) referred to hereinbefore.

Now, a production of amythiamicin A by the fermentation is illustrated with reference to the following Referential Example 1. Further, the production of amythiamicin D by methanolysis of amythiamicin A is illustrated with reference to Referential Example 2 below.

REFERENTIAL EXAMPLE 1

110 ml-portions of a seed culture medium comprising 2.0% glycerol, 2.0% dextrin, 1.0% polypeptone, 0.3% yeast extract, 0.2% ammonium sulfate, 0.2% calcium carbonate and 0.01% silicone oil (as a defoaming agent) (pH 7.4) were poured in 500-ml Erlenmyer flasks and then sterilized at 120° C. for 20 minutes. To the medium so sterilized was inoculated a loopful amount of Amycolatopsis sp. MI481-42F4 strain (deposited under FERM BP-6023 under Budapest Treaty) which had been incubated on an agar slant. The so inoculated culture medium was incubated at 27° C. for 3 days on a rotary shaker. The resulting fermentation broth was used as inoculum. 2 ml-portions of this inoculum were transferred into flasks containing 110 ml-portions of a culture medium having the same composition as that of the above-mentioned seed culture medium, followed by effecting the cultivation of the MI481-42F4 strain at 27° C. for 4 day with aeration. In this way, the desired amythiamicin A was produced and accumulated in the resultant fermentation broth.

The fermentation broth so obtained (pH 8.2, 10.1 liters) was centrifuged to separate the supernatant and the mycelial cake. The mycelial cake was extracted with methanol (5 liters). The methanolic extract was concentrated and then methanol was distilled off from the concentrated solution under reduced pressure. The residue obtained was mixed with water (5 liters) and the resulting mixture was extracted with an equal volume of butanol. The butanol extract was concentrated and the concentrate was mixed with methanol to produce a precipitate which was then separated and dried. Thus, a dried powder (4.3 g) was obtained.

This powder was dissolved in dimethylformamide, and the resulting solution was passed through a column of Sephadex LH-20 (a product of Pharmacia Co,) which had been packed with aid of dimethylformamide and which had dimensions of 50 mm in outer diameter by 1000 mm in height. The gel filtration was effected by developing this column with dimethylformamide. The effluent from the column was collected in fractions, and such active fractions having an antibacterial potency against *Bacillus thermophilus* were recovered and concentrated under reduced pressure. The residue obtained was dissolved in dimethylformamide and the dimethylformamide solution was subjected to a gel filtration on a column of a gel filtration agent, "Toyopal HW-40" (a product of Toso Co., Japan), which had been packed with aid of dimethylformamide and which had dimensions of 40 mm in outer diameter by 420 mm in height. The gel filtration was effected using dimethylformamide as the developement solvent. The active fractions of the effluent were collected and concentrated to dryness under reduced pressure to afford 780 mg of a dry powder.

This powder was dissolved in chloroform (15 ml) and the resulting solution was charged into a column of a silica gel (Art 7734 a product of Merck Co.,) (25 g) which was packed with aid of chloroform. The silica gel column was then washed with 200 ml of chloroform and then eluted with a mixture of chloroform-methanol (10:1). The antibacterially active fractions of the eluate were collected and concentrated to dryness under reduced pressure, thereby to afford a colorless powder (232 mg) which consisted of a pure product of amythiamicin A.

REFERENTIAL EXAMPLE 2

Amythiamicin A (1.0 g) obtained in Referential Example 2 above was dissolved in 100 ml of anhydrous methanol containing 5% hydrogen chloride, and the resulting solution was refluxed at 80° C. for 2 hours to effect methanolysis of amythiamicin A. The reaction solution was then concentrated to dryness under reduced pressure to remove the hydrogen chloride therefrom. The resulting powder (1.123 g) was dissolved in 5 ml of methanol and the methanolic solution was mixed with 6 g of a silica gel (Art 7734, a product of Merck Co.,).

The resultant mixture comprising the silica gel was dried under reduced pressure and the dried silica gel mass obtained was placed on the top of a column (32 mm in inner diameter by 100 mm in height) containing 25 g of silica gel (Art 7734) which had been packed with aid of chloroform. This silica gel column with said dried silica gel mass was washed with a mixture of chloroform-methanol (50:1) and then eluted with a mixture of chloroform-methanol (10:1). The effluent from the column was concentrated to dryness under reduced pressure and the residue was dissolved in chloroform. The resulting solution in chloroform was allowed to stand and cooled to deposit a crystalline and pure product of amythiamicin D. Yield 531 mg.

Amythiamicin D acid of the formula (B) above may prepared from amythiamicin D by mixing a solution of amythiamicin D in methanol (9 part) with a 1 N aqueous sodium hydroxide solution (1 part), allowing the resultant mixture to stand at room temperature for 2 hours for alkaline hydrolysis of amythiamicin D, and mixing the resulting reaction solution with 1 N hydrochloric acid (1 part) for neutralization. The resultant solution was evaporated to dryness and the residue was added with water and chloroform. The resulting chloroform extract was separated and concentrated to dryness under reduced pressure, followed by purifying the resultant powder by appropriate chromatographic procedures to give a pure product of amythiamicin D acid.

We claim:

1. An amide derivative of amythiamicin represented by the following general formula (I)

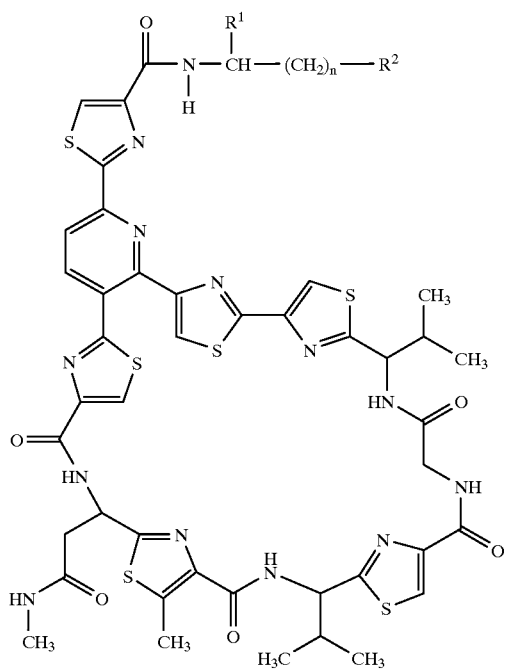

(I)

wherein n is an integer of 1 to 6, $R^1$ is a hydrogen atom, a carboxyl group or a hydroxylmethyl group, and $R^2$ is a group of the formula —$COOR^3$ where $R^3$ is a hydrogen atom or a lower alkyl group or a benzyl group of which phenyl ring may optionally be substituted by a halogen or a hydroxyl group, or $R^2$ is a group of the formula —$NR^4R^5$ where $R^4$ is a hydrogen atom or a lower alkyl group and $R^5$ is a hydrogen atom, a lower alkyl group, 3-aminopropyl group, 3-[2-(p-chloro or bromophenyl)ethyl]aminopropyl group or 3-(n-butylamino)propyl group, or $R^2$ is a methyl group, a hydroxyl group or a guanidino group of the formula —NH—C(=NH)—$NH_2$, or a pharmaceutically acceptable salt or ester thereof.

2. A derivative according to claim 1, which is a compound of the formula (Ia)

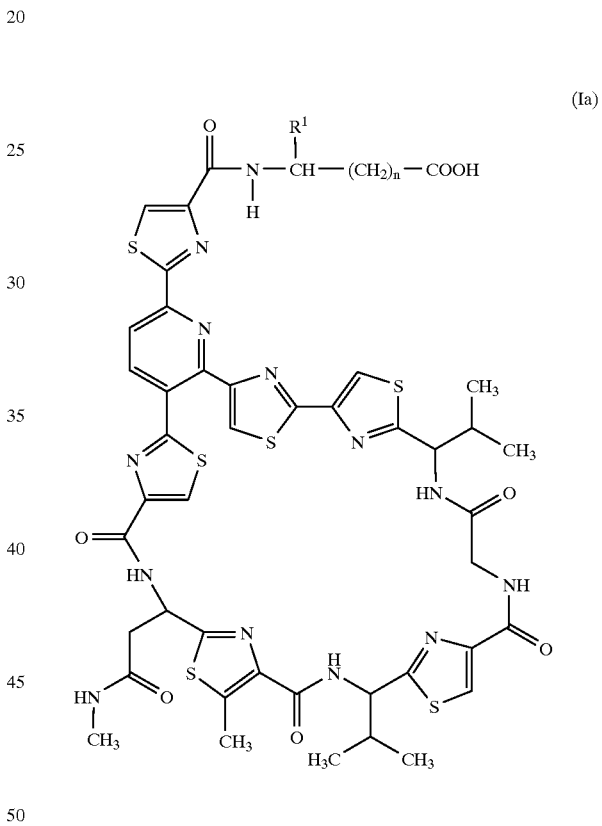

(Ia)

wherein n is an integer of 1 to 6 and $R^1$ is a hydrogen atom, a carboxyl group or a hydroxymethyl group, or a pharmaceutically acceptable salt thereof or a lower alkyl ester or a benzyl ester thereof.

3. A derivative according to claim 2, which is a compound of the formula (Ia-1)

23

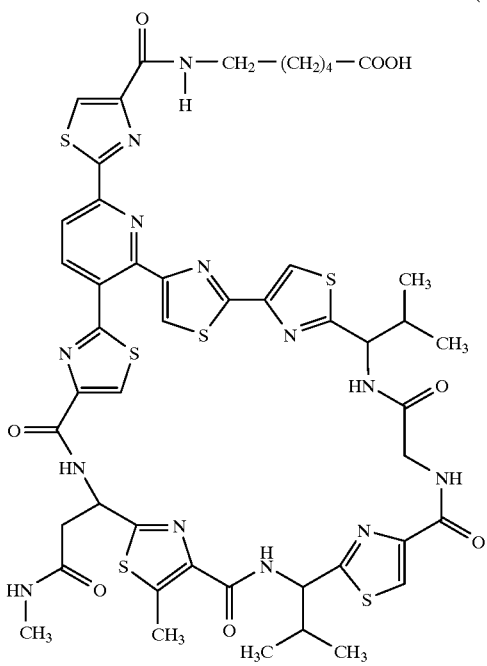
(Ia-1)

or a pharmaceutically acceptable salt thereof or a lower alkyl ester or a benzyl ester thereof.

4. A derivative according to claim 1, which is a compound of the formula (Ib)

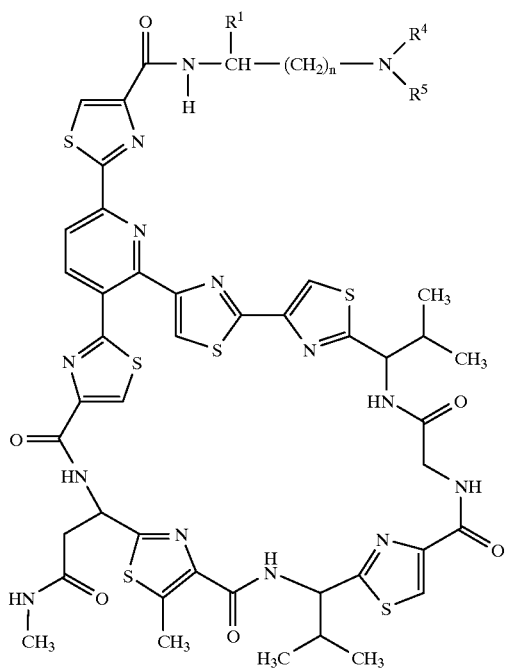
(Ib)

wherein n is an integer of 1 to 6, $R^1$ is a hydrogen atom, a carboxyl group or a hydroxymethyl group, and $R^4$ is a hydrogen atom or a lower alkyl group and $R^5$ is a hydrogen atom, a lower alkyl group, 3-amino-propyl group, 3-[2-(p-chloro or bromo-phenyl)ethyl]aminopropyl group or 3-(n-butylamino)propyl group, or a pharmaceutically acceptable salt or ester thereof.

5. A derivative according to claim 4, which is a compound of the formula (Ib-1)

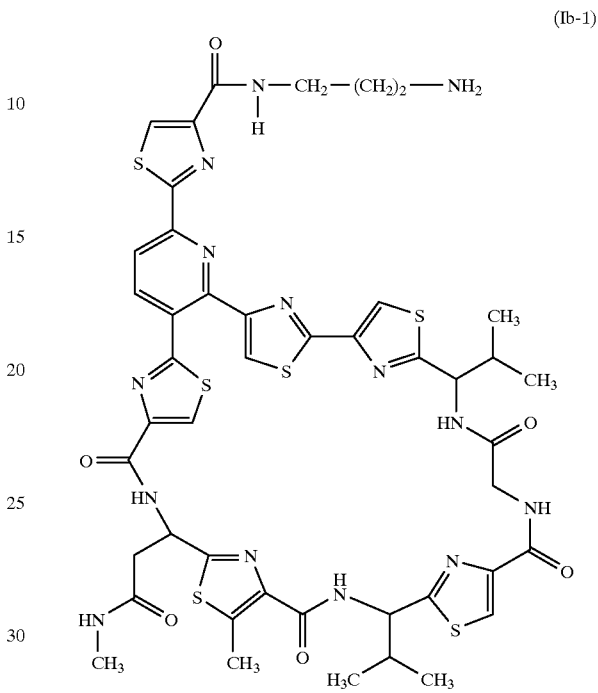
(Ib-1)

or a pharmaceutically acceptable salt thereof.

6. A derivative according to claim 1, which is a compound of the formula (Ic)

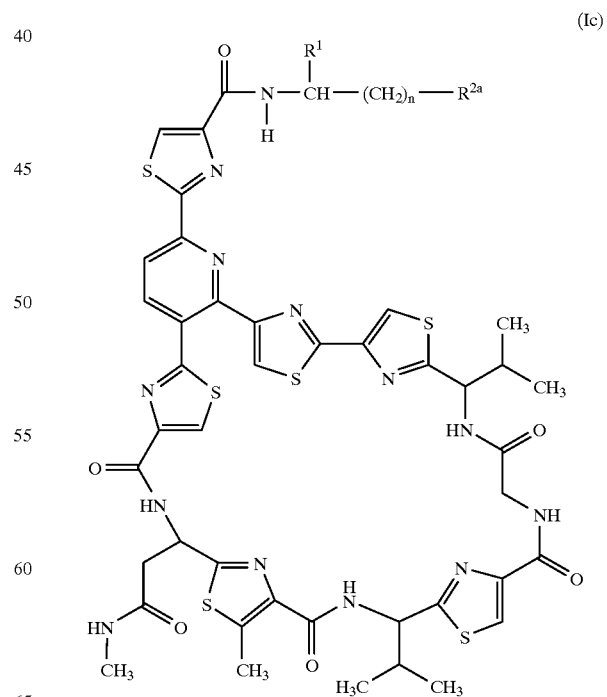
(Ic)

wherein n is an integer of 1 to 6, $R^1$ is a hydrogen atom, a carboxyl group or a hydroxymethyl group and $R^{2a}$ is a methyl group or a hydroxyl group, or a pharmaceutically acceptable salt or ester thereof.

7. A derivative according to claim 6, which is a compound of the formula (Ic-1)

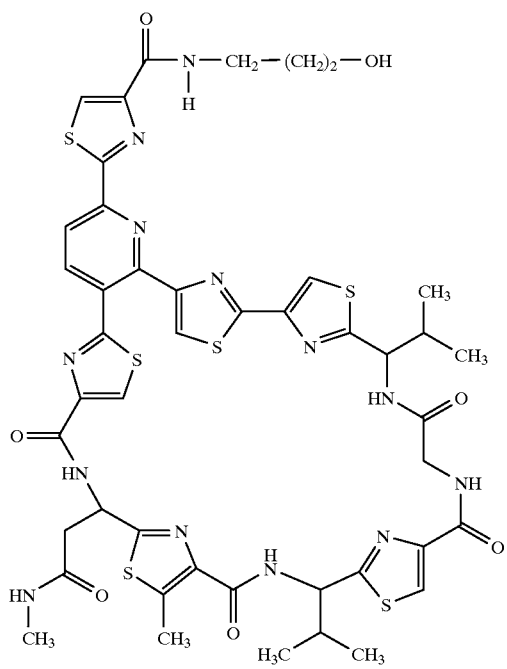

(Ic-1)

8. A derivative according to claim 1, which is a compound of the formula (Id)

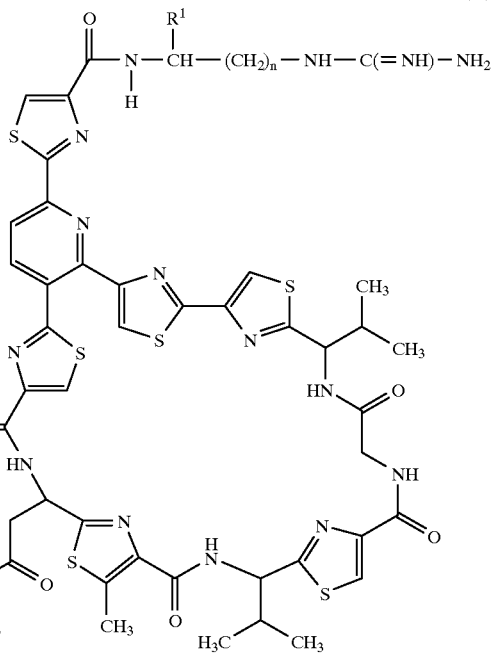

(Id)

wherein n is an integer of 1 to 6, and $R^1$ is a hydrogen atom, a carboxyl group or a hydroxymethyl group; or a pharmaceutically acceptable salt or ester thereof.

9. A pharmaceutical composition which comprises an amount of the amide derivative of amythiamicin having the formula (I) as defined in claim 1 as an active ingredient, in association with a pharmaceutically acceptable carrier for the active ingredient.

10. A pharmaceutical composition according to claim 9, which is an antibacterial composition comprising an antibacterially effective amount of the amide derivative of amythiamicin having the formula (I) as defined in claim 1.

11. A method for the manufacture of a pharmaceutical composition, particularly an antibacterial composition, which comprises mixing an amide derivative of amythiamicin having the formula (I) as defined in claim 1, with a pharmaceutically acceptable solid or liquid carrier.

12. A method of treating bacterial infection by administering an anti-bacterial effective amount of an amide derivative according to claim 1.

13. The method of claim 12, wherein said bacterial infection is caused by a gram positive bacteria.

14. The method of claim 13, wherein said gram positive bacteria is caused by a methicillin-resistant *Staphylococcus aureus*.

* * * * *